US008945022B2

(12) United States Patent
Konya et al.

(10) Patent No.: US 8,945,022 B2
(45) Date of Patent: *Feb. 3, 2015

(54) PUNCTURING SYSTEM

(75) Inventors: Ahmet Konya, Waldsee (DE); Klaus Schoettle, Willstaett (DE); Herbert Harttig, Neustadt (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 785 days.

This patent is subject to a terminal disclaimer.

(21) Appl. No.: 12/577,570

(22) Filed: Oct. 12, 2009

(65) Prior Publication Data

US 2010/0049092 A1    Feb. 25, 2010

Related U.S. Application Data

(63) Continuation of application No. PCT/EP2008/002172, filed on Mar. 19, 2008.

(30) Foreign Application Priority Data

Apr. 12, 2007    (EP) .................................... 07007470

(51) Int. Cl.
*A61B 5/15* (2006.01)
*A61B 5/151* (2006.01)
(Continued)

(52) U.S. Cl.
CPC ........... *A61B 5/1411* (2013.01); *A61B 5/15146* (2013.01); *A61B 5/14532* (2013.01); *A61B 2562/0295* (2013.01)
USPC ........................... 600/583; 600/584; 606/181

(58) Field of Classification Search
CPC ........... A61B 5/1411; A61B 5/150206; A61B 5/15029; A61B 5/15103; A61B 5/15115; A61B 5/15117; A61B 5/15146; A61B 5/15165; A61B 5/15169; A61B 5/15171; A61B 2562/0295
USPC ........................... 600/583, 587, 584; 606/181
See application file for complete search history.

(56) References Cited

U.S. PATENT DOCUMENTS 3,716,292 A * 2/1973 Long .............................. 352/225
8,496,602 B2 * 7/2013 Harttig et al. ................. 600/584
(Continued)

FOREIGN PATENT DOCUMENTS

DE    2 803 345 B1    6/1979
EP    1360935 B1    12/2006
(Continued)

OTHER PUBLICATIONS

English Translation of the corresponding PCT/EP2008/002172 International Report on Patentability.
(Continued)

*Primary Examiner* — Lee S Cohen
*Assistant Examiner* — Emily Lloyd
(74) *Attorney, Agent, or Firm* — Woodard, Emhardt, Moriaty, McNett & Henry LLP

(57) ABSTRACT

A puncturing system for obtaining a sample of body fluid comprises a magazine that comprises a lancet carrier that carries several lancets, a puncturing device comprising a compartment for the magazine, an incremental advancing mechanism for moving the lancets successively to a puncturing position, and a puncturing drive for accelerating one of the lancets that is positioned in the puncturing position in a puncturing motion. The magazine comprises a coupling facility with a receptacle for the lancet carrier. The receptacle is mobile with respect to a magazine housing The lancets that are carried by the lancet carrier can be moved relative to the receptacle by actuating the incremental advancing mechanism The receptacle is adapted to couple the puncturing drive to one of the lancets positioned in the puncturing position for transmitting a driving force generated by the puncturing drive during a puncture to the lancet positioned in the puncturing position.

14 Claims, 4 Drawing Sheets

(51) Int. Cl.
*A61B 5/155* (2006.01)
*A61B 5/157* (2006.01)
*A61B 5/145* (2006.01)

(56) References Cited

U.S. PATENT DOCUMENTS

| | | |
|---|---|---|
| 2003/0083686 A1 | 5/2003 | Freeman et al. |
| 2003/0199906 A1 | 10/2003 | Boecker et al. |
| 2003/0211619 A1 | 11/2003 | Olson et al. |
| 2005/0245845 A1* | 11/2005 | Roe et al. .................. 600/583 |
| 2005/0245954 A1 | 11/2005 | Roe et al. |
| 2006/0264996 A1 | 11/2006 | LeVaughn et al. |
| 2007/0038150 A1* | 2/2007 | Calasso et al. .............. 600/583 |
| 2009/0287116 A1 | 11/2009 | Konya |
| 2014/0005510 A1* | 1/2014 | Harttig et al. .............. 600/365 |

FOREIGN PATENT DOCUMENTS

| | | |
|---|---|---|
| WO | 2005/018711 A1 | 3/2005 |
| WO | 2005/104948 A1 | 11/2005 |
| WO | 2005/107596 A2 | 11/2005 |
| WO | 2008/083844 A1 | 7/2008 |

OTHER PUBLICATIONS

DE 2 803 345 B1 English Language Translation.

* cited by examiner

PUNCTURING SYSTEM

CROSS-REFERENCE TO RELATED APPLICATIONS

This application is a continuation of PCT/EP2008/002172, filed Mar. 19, 2008 which is based on and claims priority to EP 07007470.3, filed Apr. 12, 2007 which are hereby incorporated by reference in their entirety.

BACKGROUND OF THE INVENTION

1. Field of the Invention

The present invention relates to the field of puncturing devices adapted for use in obtaining body fluid samples.

2. Description of Related Art

Puncturing systems adapted for use in obtaining body fluid samples are used, for example, by diabetics who need to check their blood sugar level multiple times daily and who need a sample of body fluid, usually blood or interstitial fluid, obtained via a puncturing wound that is generated with a puncturing system.

A puncturing system of this type can include a magazine that contains a lancet carrier that carries several lancets, and a puncturing device having a compartment for a magazine of this type, an incremental advancing mechanism for moving the lancets of a magazine that is inserted into the compartment to a puncturing position in a sequential manner, and a puncturing drive for accelerating a lancet that is positioned in the puncturing position for a puncturing motion.

In puncturing systems of this type, a transmission of force from the puncturing drive to a lancet that is positioned in the puncturing position must occur by means of adequate coupling. Known coupling means are complex, require much mechanical effort, and necessitate fabrication at low tolerances such that the associated costs are substantial.

There has thus been a need in the art to devise a way in which a cost-efficient puncturing system of the type specified above can be created.

BRIEF SUMMARY OF THE INVENTION

It is against the above background that the present invention provides certain unobvious advantages and advancements over the prior art. In particular, the inventors have recognized a need for improvements in puncturing systems. Although the present invention is not limited to specific advantages or functionality, it is noted that one embodiment of the present invention is based on a puncturing system having the features set forth in claim 1. Advantageous further developments of the invention are the subject matter of the remainder of the claims.

In a puncturing system according to the invention, the puncturing drive is not coupled directly to a lancet. Instead, the puncturing drive is coupled to a lancet that is positioned in the puncturing position by means of a coupling facility of the magazine which, in operation, couples the puncturing drive to a lancet that is positioned in the puncturing position. By this means, the mechanical effort involved in coupling the lancet drive to the lancet destined to be used for puncturing can be reduced.

For example, the coupling facility of the magazine can be coupled to the puncturing drive already upon insertion of the magazine into the magazine compartment of the puncturing device. Correct positioning of the coupling facility with respect to a lancet that is positioned in the puncturing position or to the lancet carrier can be effected already during the manufacture of the magazine such that the coupling facility of the magazine can be coupled to the lancet without any contribution from the user. Especially in the case of ribbon-shaped lancet carriers, this allows for reliable coupling to the puncturing drive with very little effort such that it can accelerate a lancet for a puncturing motion.

The coupling facility is preferably coupled to the lancet carrier such that during a puncturing motion the lancet carrier is moved in conjunction with a puncturing lancet. A transmission of the driving force generated by a lancet drive from the coupling facility to the lancet positioned in the puncturing position is effected very easily via the lancet carrier. This is the case, since the lancet carrier can maintain a defined position relative to the coupling facility even upon actuation of the incremental advancing mechanism that is used to convey fresh lancets of the lancet carrier into the puncturing position. The coupling facility can therefore couple to the lancet carrier for another puncture with relatively little effort after each actuation of the incremental advancing mechanism or even be coupled permanently to the lancet carrier, i.e. remain coupled to the lancet carrier even during actuation of the incremental advancing mechanism. Likewise, reliable coupling between the coupling facility of the magazine and the puncturing drive can be realized with little effort as well, since the motions of the lancet carrier effected by the incremental advancing mechanism can be effected without influencing the puncturing drive and the coupling facility of the magazine. This is advantageous in that it does not require the parts participating in the coupling of the puncturing drive to be repositioned with much effort after each puncture or to ensure correspondingly exact positioning and coupling after each actuation of the incremental advancing mechanism by means of complex and cost-intensive measures.

These and other features and advantages of the present invention will be more fully understood from the following detailed description of the invention taken together with the accompanying claims. It is noted that the scope of the claims is defined by the recitations therein and not by the specific discussion of features and advantages set forth in the present description.

BRIEF DESCRIPTION OF THE SEVERAL VIEWS OF THE DRAWING

The following detailed description of the embodiments of the present invention can be best understood when read in conjunction with the following views of the drawing. The features described in the process can be made the subject matter of claims either alone or in combination. Identical and equivalent components of various exemplary embodiments are identified by consistent reference numbers in the drawings. In the drawing figures:

Skilled artisans will appreciate that elements in the figures are illustrated for simplicity and clarity and have not necessarily been drawn to scale. For example, the dimensions of some of the elements in the figures may be exaggerated relative to other elements to help improve understanding of the embodiments of the present invention.

DETAILED DESCRIPTION OF THE INVENTION

For the purposes of describing and defining the present invention it is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

Figure 1:
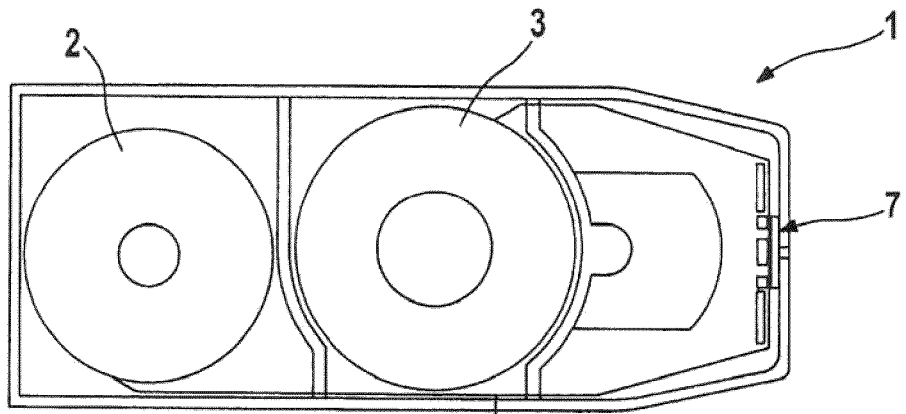
FIG. 1 shows a schematic top view of an exemplary embodiment of a magazine that contains a ribbon-shaped lancet carrier with several lancets.
Figure 2:
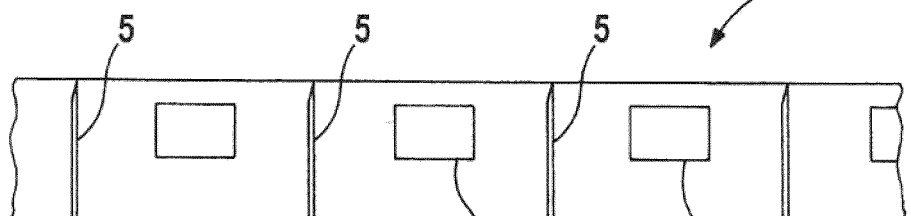
FIG. 2 shows an exemplary embodiment of a lancet carrier with lancets and test fields.

FIG. 1 shows a magazine 1 that contains two rollers 2, 3 onto which is reeled a ribbon-shaped lancet carrier 4 that is shown schematically in FIG. 2. In this context, the first roller 2 carries sections of the lancet carrier 4 with unused lancets 5 and the second roller 3 carries spent sections of the lancet carrier 4. If the magazine 1 shown in FIG. 1 is inserted into a magazine compartment 25 of a puncturing device 20, the second roller 3, onto which spent sections of the lancet carrier 4 are reeled, is driven by an incremental advancing mechanism 26 of the puncturing device 20 in order to sequentially convey the lancets 5 contained in the magazine 1 into a puncturing position. In the puncturing position, a lancet 5 is positioned such that, once a puncturing motion is effected by the puncturing drive 11 of the puncturing device 20, it generates in a user's body part that is pressed against it a puncturing wound from which a sample of body fluid can be obtained for diagnostic purposes. By actuating the incremental advancing mechanism, the driven roller 3 of the magazine 1 can be rotated to the extent that a fresh lancet 5 of the lancet carrier 4 reaches the puncturing position for a puncture.

According to FIG. 2, the lancers 5 are arranged on the ribbon-shaped lancet carrier such as to be transverse to its longitudinal direction. Situated between two lancers 5 there is one test field 6 each for testing a sample of body fluid that is obtained from a puncturing wound. For photometric determination of an analyte concentration, the test fields 6 can contain test chemicals that effect a concentration-dependent color change. However, it is also feasible to set up the test fields 6 for electrochemical or spectroscopic testing of a sample of body fluid.

Figure 3:
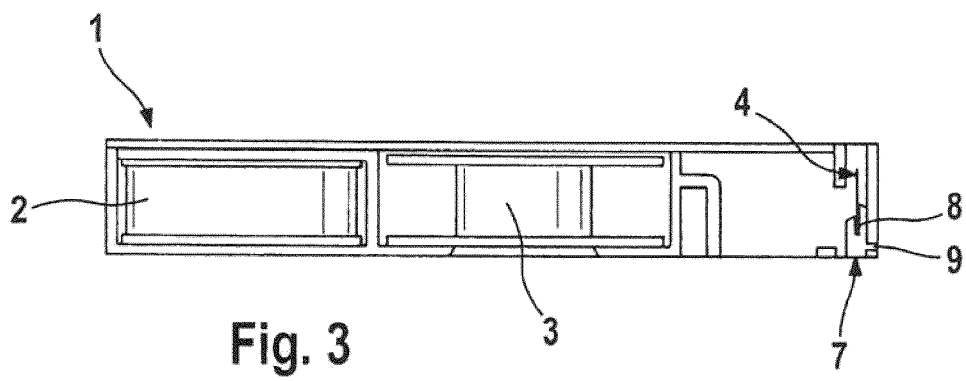
FIG. 3 shows a side view related to FIG. 1 before a puncture.
Figure 4:
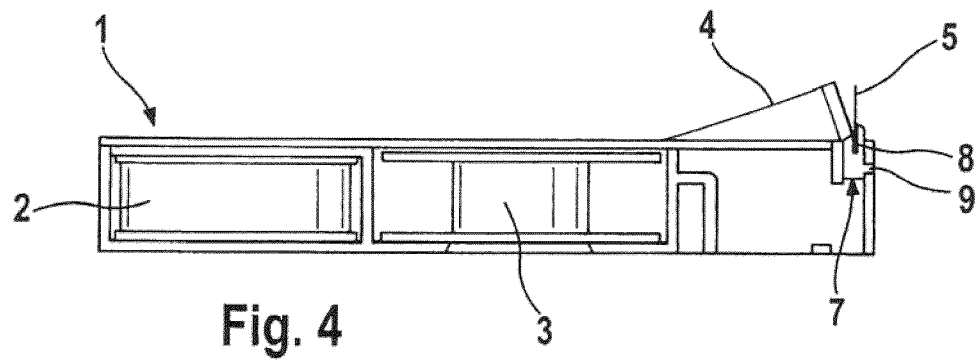
FIG. 4 shows a view according to FIG. 3 during a puncture.

Shown in a top view in FIG. 1 and in a side view in FIGS. 3 and 4, the magazine 1 has a coupling facility 7 relative to which the lancets 5 carried by the lancet carrier 4 are movable by means of actuation of the incremental advancing mechanism. In operation, the coupling facility 7 couples the puncturing drive of a puncturing device to a lancet 5 that is positioned in the puncturing position. The coupling facility can thereby transmit a driving force that is generated during a puncture by the puncturing drive 11 to the lancet 5 positioned in the puncturing position. In the embodiment shown, the coupling facility 7 couples the puncturing drive of a puncturing device to the lancet carrier 4 such that, during a puncture, the lancet carrier 4 is moved in conjunction with a lancet 5 that is positioned in the puncturing position.

The coupling facility 7 has a receptacle 8 for the lancet carrier 4. In the example shown, the receptacle has the form of a slit. The receptacle 8 is pant of a sled that can be driven in the direction of puncturing relative to a magazine housing. Via the receptacle 8, the coupling facility 7 is coupled permanently to the lancet carrier 4. Advantageously, the coupling facility 7 therefore remains coupled to the puncturing drive even during actuation of the incremental advancing mechanism such that mechanical adjustment to the incremental advancing mechanism is not required.

During a puncture, the coupling facility 7 is driven by the lancet drive in the direction of puncturing from the position shown in FIG. 3 to the position shown in FIG. 4 in an advancing phase and moved back to the position shown in FIG. 3 in a subsequent returning motion. For coupling to the puncturing drive, the coupling facility 7 has a coupling element 9, in the form of a peg in the exemplary embodiment shown, which engages a matching coupling element of the puncturing drive in the manner of a positive fit.

The driving force generated during a puncture by a coupled puncturing drive effects a motion of the coupling facility 7, including the tape section of the lancet carrier 4 that is positioned inside the slit 8, in the direction of puncturing. A bending facility, which is not shown and can optionally be arranged on the magazine or on the puncturing device, can effect bending of the lancet carrier tape 4 as shown in FIG. 4. Thereby the tip of the lancet 5 positioned in the puncturing position lifts off from the surface of the ribbon-shaped lancet carrier 4 and, without being impeded by the ribbon-shaped lancet carrier 4, can puncture into a body part of a user that is touched against it. The bending facility can be provided, for example, in the form of two fork prongs that stand oblique relative to the direction of puncturing and between which a lancet protrudes during a puncture, whereby the fork prongs hold back and bend the lancet carrier ribbon on both sides next to the lancet.

After a puncture, the incremental advancing mechanism of a puncturing device can be actuated to position a test element 6 of the ribbon-shaped lancet carrier 4 in the slit 8 of the coupling facility 7. By actuating the puncturing drive again, the test field 6 can then be shifted to a puncturing wound generated by the preceding puncture and the test field 6 can take up a sample of body fluid.

Figure 5:
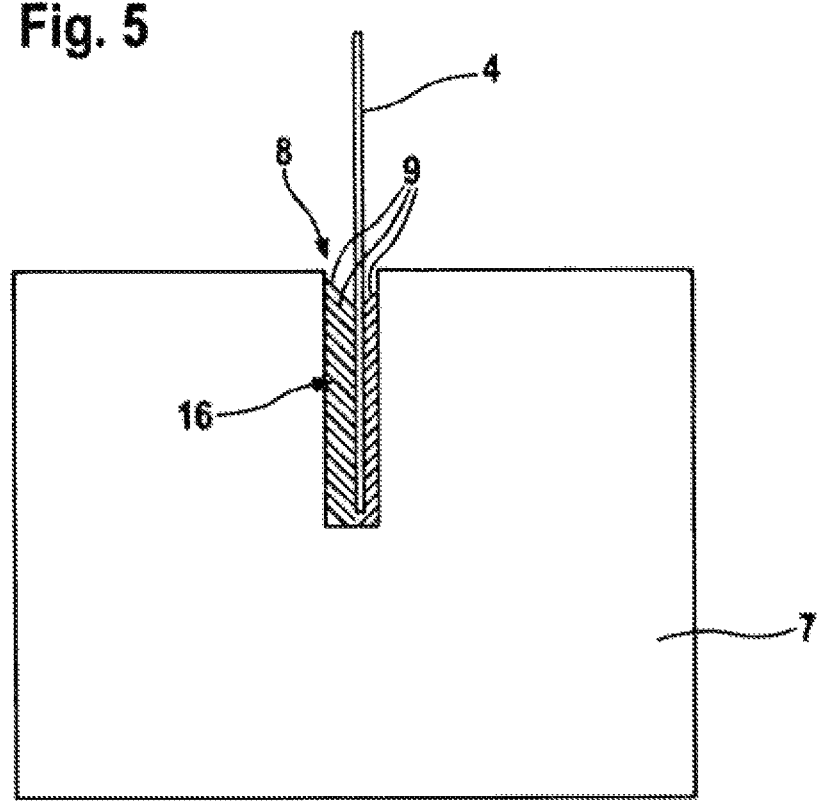
FIG. 5 shows a schematic detailed view related to FIG. 3.

FIG. 5 shows schematically a detail of the coupling facility 7 of the embodiment described above. As is evident from the figure, the walls of the receptacle 8 that is provided in the form of a slit are covered with fibers standing in oblique direction, for example bristles 9. The bristles 9 are arranged such that their free end is oriented to be oblique relative to the returning direction. Thereby, the lancet carrier 4 is held by the bristles 9 during a returning motion of the coupling facility 7 and can be retracted better, in conjunction with the coupling facility 7, by a puncturing drive coupled to it. Accordingly, in the exemplary embodiment shown, the coupling facility 7 contacts the lancet carrier 4 via a structured coupling surface 16 that poses a resistance against a relative motion of the lancet carrier 4 versus the coupling surface 16 as a function of the direction of the relative motion.

A coupling surface of this type impedes the transport of the lancet carrier 4 effected by the incremental advancing mechanism either not at all or only little since the structured surface effects increased friction only in the direction of the returning motion. During the returning motion, the structured surface of the coupling surfaces 16 of the receptacle 8, i.e. of the opposite side walls of the slit 8 in the exemplary embodiment shown, causes improved adhesion of the lancet carrier 4 within the receptacle 8 though. The lancet carrier 4, in conjunction with the coupling facility 7, can therefore be retracted quickly and a lancet 5 carried by the lancet carrier 4 can be retracted from the puncturing wound just generated.

A structured surface with such advantageous properties can be attained not only by means of the fibers 9 shown in FIG. 4, but also by other projections, elevations or recesses of the coupling surface of the receptacle 8 that contact the surface of the lancet carrier 4.

A structured surface according to FIG. 5 can be attained, for example, by means of coating with staple fibers in parallel-orientation. The fibers 9 are secured in a fixation layer. They are oriented at an angle of between 30.degree. and 90.degree., preferably 45.degree. to 75.degree., with respect to the coupling surface 16 of the receptacle 8. In this context, the fibers are inclined towards the bottom of the slit, i.e. in the direction of the returning motion and therefore in the direction, into which a force is to be exerted on the lancet carrier 4 by the coupling surface 16, as is shown in FIG. 5.

The transport of the lancet carrier 4 between two coupling surfaces of this type of structure proceeds with advantageously little friction. The insertion of a ribbon-shaped lancet carrier 4 into the receptacle 8 also causes only minimal friction. However, attempting to move the lancet carrier 4 against the direction of inclination of the fibers 9, these lodge onto even the smallest uneven sites and thus hold the lancet carrier 4 back. For example a flock fiber film can be used as structured coupling surface with inclined fibers 9 and applied to the coupling facility, in particular by gluing it to the coupling facility.

A suitable flock fiber film can be manufactured as follows, for example. A polyester film, for example made of Hostaphan RN50 made by Mitsubishi Polyester Film, Wiesbaden, is coated with a conductive adhesive, for example Mecoflock D453/5-09 made by Kissel+Wolf GmbH, Wiesloch, Germany. The adhesive layer is then flocked with polyamide flock of 1.7 dtex and a length of 0.5 mm using an Ero-Mini flocking device made by Maag Flockmaschinen GmbH, Gommeringen, Germany. Flock of this type is available from Swissflock, Stuttgart, Germany. Right after flocking, the film is pulled through a calender in which the roll gap is set to 360 µm, for example. This causes the fibers to take on an oblique orientation. After drying, the flock layer is vacuumed and thus cleaned by removing loose fibers. The fibers then have an angle with respect to the polyester film of approx. 45° in the direction of rolling. The fibers are oriented, on average, perpendicular to the direction of rolling.

Another option for manufacture of a suitable flock fiber film is to parallel-bend a plastic film up and down in an alternating manner at distances of, for example, 10 mm such that the kinks each include angles of 100° to 140°, for example 120°. Then the flocks are applied to the film like in the preceding example, but the film is not transported through a roll gap thereafter. This is the case since the fibers are shot into the adhesive in an oblique orientation, due to the inclination of the sections of film, and thus are positioned at an angle of approx. 60 to 70° with respect to the film.

The groove of the coupling facility 7 shown in FIG. 5 can have a width of 0.8 mm, for example. Flock fiber film can be glued to the walls of the slit, for example, using an epoxy adhesive such that the fibers 9 point in the direction of the bottom of the slit according to FIG. 5.

Figure 6:
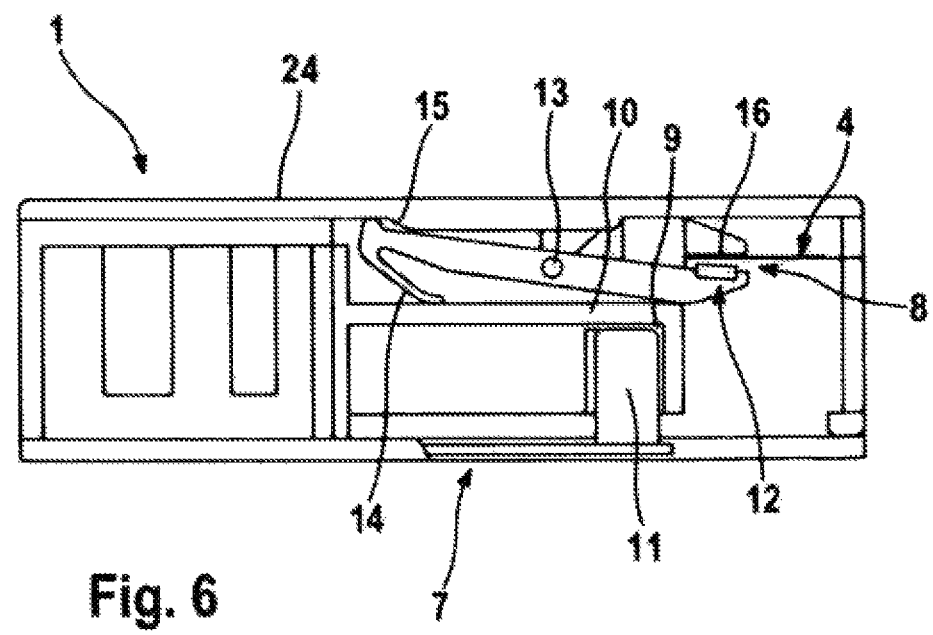
FIG. 6 shows a sectional view of a detail of another exemplary embodiment of a magazine.

FIG. 6 shows another exemplary embodiment of a magazine 1 having a coupling facility 7. Like the magazine 1 shown in FIG. 1, the magazine 1 shown in FIG. 6 contains a ribbon-shaped lancet carrier 4 with several lancets 5 in an arrangement according to FIG. 2. This magazine 1 differs from the preceding embodiment described above essentially only in the design of the coupling facility 7, which, in operation, couples the puncturing drive of a puncturing device to the lancet carrier 4 in order to transfer, during a puncture, a driving force generated by the puncturing drive to a lancet 5 positioned in the puncturing position.

The coupling facility 7 comprises a sled 10 that is borne such that it can be shifted with respect to a magazine housing 24. The sled 10 has a coupling element for coupling to the puncturing drive of a puncturing device a recess 9 that is engaged by the puncturing drive 11 by means of a peg such that the sled 10 can be shifted in the direction of puncturing by a driving force that is generated by the puncturing drive 11.

For coupling to the lancet carrier 4, the coupling facility 7 shown has a receptacle 8 through which the lancet carrier 4 is guided. The receptacle 8 is formed by the coupling surface 16 that is rigidly arranged on the sled 10 and a press-against element 12 that is mobile with respect to the coupling surface 16 and clamps the lancet carrier 4 inside the receptacle during a puncture and releases it again after a puncturing and a returning motion have been completed.

The press-against element 12 is borne on the sled 10 such that it can be rotated about a pivot point 13. A spring element 14 presses the back end of the press-against element 12 against a connecting member 15 which is integrated into the magazine housing 11 in the embodiment shown. Moving the sled 10 in the direction of puncturing causes the back end of the press-against element 12 to run along the connecting member 15 and thus, due to it being borne such that it can be rotated, perform a closing motion that presses its front end against the coupling surface 16 of the sled 10 such that the lancet carrier 4 is clamped between the coupling surface 16 and the front end of the press-against element 12. By this means, the coupling facility 7 of the exemplary embodiment shown grasps the lancet carrier 4 in a clamping manner during a puncture and releases it again after puncturing and returning motion are completed. Clamping the lancet carrier 4 inside the receptacle 8 allows the lancet carrier 4 to be retracted quickly and reliably during a returning motion such that a lancet carried by the carrier can be quickly pulled out of a puncturing wound thus generated, which is important for the puncturing to be associated with as little pain as possible.

In the embodiment shown, the clamping force for clamping the lancet carrier 4 is effected by the spring element 14 that presses the back end of the press-against element 12 against the connecting member 15 which defines the closing motion of the press-against element 12 during a puncturing motion.

Figure 7:
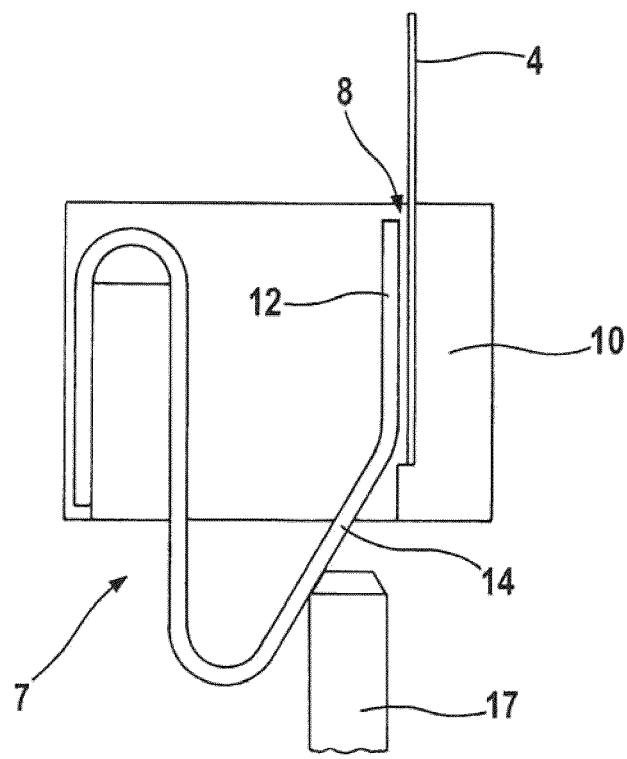
FIG. 7 shows a schematic detailed view of another exemplary embodiment of a coupling facility of a magazine with a ribbon-shaped lancet carrier.
Figure 8:
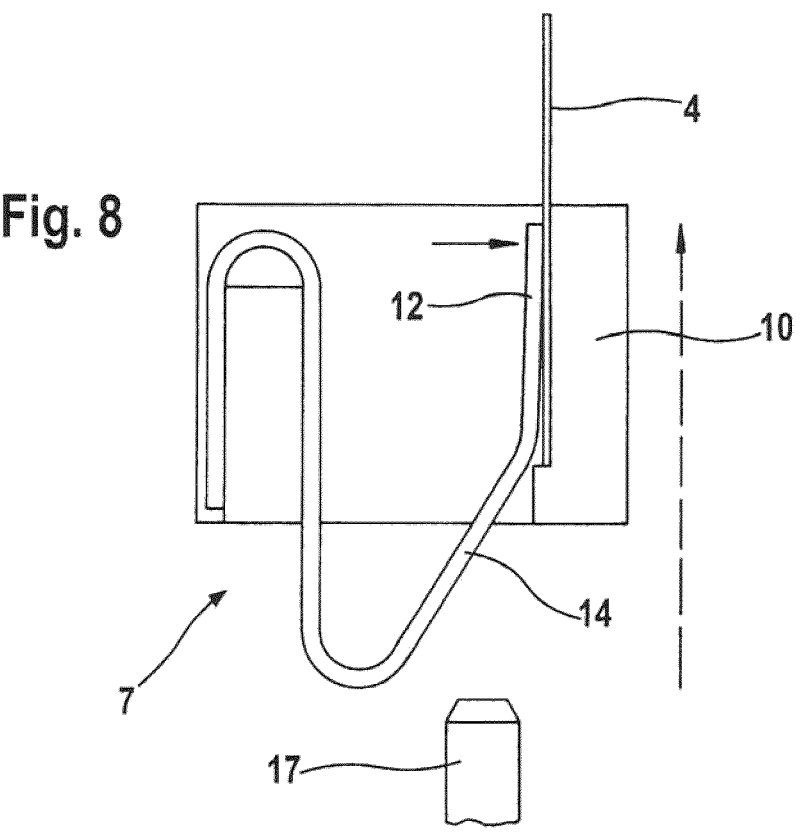
FIG. 8 shows a detailed view according to FIG. 7 during a puncture.
Figure 9:
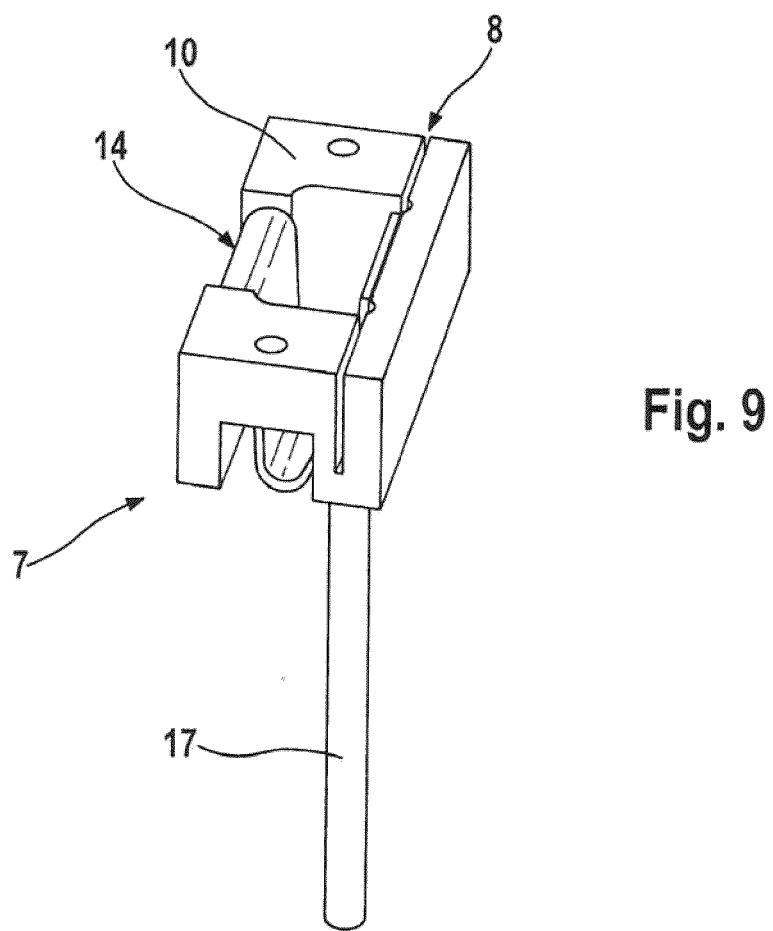
FIG. 9 shows an oblique view related to FIG. 7.

FIGS. 7 to 9 show another embodiment of a coupling facility 7 that can be used, for example in the case of a magazine 1 according to FIG. 1 or 6, in place of the preceding coupling facilities 7 shown and described above. Similar to the coupling facility 7 shown in FIG. 6, the coupling facility 7 shown in FIGS. 7 to 9 grasps the lancet carrier 4 in a clamping manner during a puncture and releases it again after a puncturing and returning motion are completed. Accordingly, FIG. 7 shows the coupling facility 7 before a puncture with a released lancet carrier 4. In FIG. 8, the lancet carrier 4 is clamped by the coupling facility 7, i.e. it is shown according to the conditions that are evident during a puncture. FIG. 9 shows an oblique view related to the part of the coupling facility 7 that is shown in FIGS. 7 and 8.

Similar to the embodiment shown in FIG. 6, the coupling facility 7 of the embodiment shown in FIGS. 7 to 9 comprises a sled 10 that can be driven in the direction of puncturing and carries a receptacle 8 through which the lancet carrier 4 is fed. The direction of puncturing is indicated by a dashed arrow in FIG. 8. The receptacle 8 for the lancet carrier 4 can, for example, be provided in the form of a slot.

The receptacle 8 interacts with a press-against element 12 that presses the lancet carrier 4 against a coupling surface of the receptacle 8 during a puncture and clamps it by this means. The clamping force for clamping the lancet carrier 4 is effected by a spring element 14 which is provided by means of the same component as the press-against element 12 in the exemplary embodiment shown. The spring element 14 interacts with an opener 17 that is arranged fixed in place with respect to the magazine housing (not shown) in the embodiment shown and can be provided, for example, in the form of a projection on the magazine housing.

If the sled 10 is in its starting position shown in FIG. 7 before a puncture, the opener 17 presses against the spring element 14 and by this means causes the receptacle 8 to open. The lancet carrier 4 can then be moved in the receptacle 8 perpendicular to the direction of puncturing by actuating the incremental advancing mechanism (not shown). Moving the sled 10 in the direction of puncturing, the spring element 14 moves away from the opener 17 such that it clamps the lancet carrier 4 in the receptacle 8. By this means, the spring force exerted by the spring element 14 presses the lancet carrier 4 against the coupling surface of the receptacle 8.

The spring element 14 can be manufactured at low cost from plastic materials. However, it is also feasible to manufacture the spring element 14 from metal.

Figure 10:
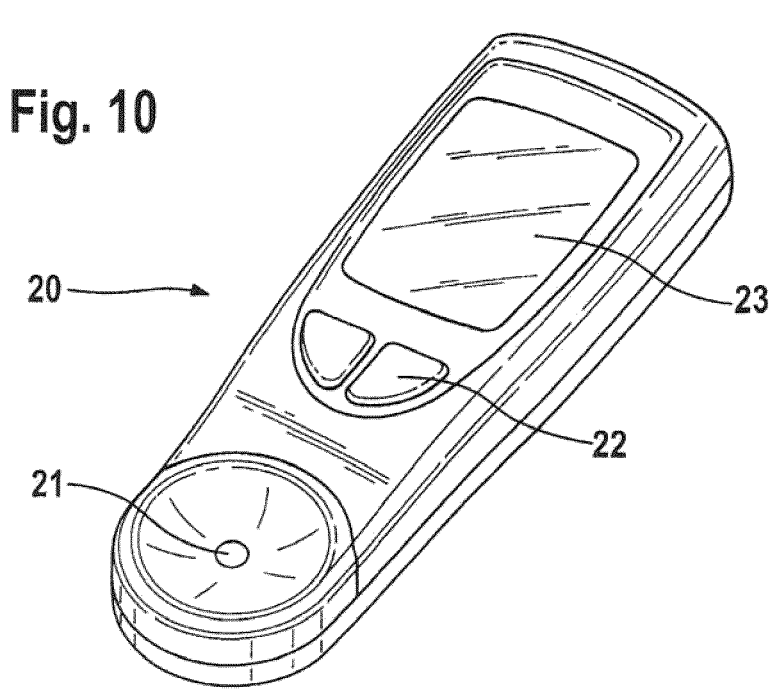
FIG. 10 shows an exemplary embodiment of a puncturing device.

FIG. 10 shows an embodiment of a puncturing device for obtaining a sample of body fluid. The puncturing device 20 has an opening 21 against which a body part is pressed for creating a puncturing wound. The puncturing device 20 further comprises operating elements 22 in the form of keys and a display facility 23 in the form of a liquid crystal display for displaying test results. The puncturing device 20 has a compartment (not shown) for receiving a magazine 1 that contains a lancet carrier 4 that carries several lancets 5. Exemplary embodiments of a magazine 1 of this type have been illustrated above by means of FIGS. 1 to 9. The compartment of the puncturing device 20 shown has an opening that can be closed and is situated on the back side of the puncturing device 20 shown.

A measuring and analytical facility (not shown) is integrated into the puncturing device 20 shown and can be used to determine the analyte concentration of a sample of body fluid. For this purpose, a sample of body fluid is taken up by a test field 6 of the lancet carrier ribbon 4 that is contained in an inserted magazine 1 (see FIG. 2) after a puncturing wound is created. Taking of a sample is done by positioning a test field 6 of the lancet carrier ribbon 4 under the device opening 21 by actuating the incremental advancing mechanism. Actuating the puncturing drive again allows the lancet carrier 4 with the test field 6 to be shifted in the direction of puncturing such that the test field 6 rests against the puncturing wound of a body part that is pressed against the device opening 21 for taking-up a sample of body fluid.

Together, the puncturing device 20 shown in FIG. 10 and a magazine 1 described by reference to FIGS. 1 to 9 form a puncturing system.

LIST OF REFERENCE NUMBERS

1 Magazine
2 Roller
3 Roller
4 Lancet carrier
5 Lancet
6 Test field
7 Coupling facility
8 Receptacle for lancet carrier
9 Coupling element/bristles
10 Sled
11 Puncturing drive
12 Press-against element
13 Pivot point
14 Spring element
15 Connecting member
16 Coupling surface
17 Opener
20 Puncturing device
21 Device opening
22 Operating element
23 Display facility
24 Magazine housing Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

The invention claimed is:

1. A puncturing system for obtaining a sample of body fluid, the system comprising:
 a magazine comprising a lancet carrier that has several lancets;
 a puncturing device comprising:
  a compartment for the magazine, and
  a puncturing drive for accelerating one of the lancets that is positioned in a puncturing position in a puncturing motion;
 wherein the magazine further comprises a coupling facility with a receptacle defining a recess in which a portion of the lancet carrier is received, said receptacle being mobile with respect to a magazine housing;
 wherein the lancets of the lancet carrier are configured to be moved relative to the receptacle;
 wherein the receptacle is adapted to couple the puncturing drive to the lancet positioned in the puncturing position for transmitting a driving force generated by the puncturing drive during a puncture to the lancet positioned in the puncturing position; and
 wherein the puncturing drive is configured to move the lancet along with the portion of the lancet carrier received in the recess by moving the receptacle in the puncturing motion during the puncture.

2. The puncturing system of claim 1 wherein the lancet carrier is ribbon-shaped.

3. The puncturing system of claim 1 wherein the lancet carrier carries test fields for testing a sample of body fluid obtained from a puncturing wound, said test fields being arranged between the lancets.

4. The puncturing system of claim 1 wherein the coupling facility is configured to couple to the lancet carrier and to move the portion of the lancet carrier received in the recess during a puncture in conjunction with the lancet that is positioned in the puncturing position.

5. The puncturing system of claim 1 wherein the coupling facility is configured to remain coupled to the puncturing drive during movement of the lancet carrier relative to the receptacle.

6. The puncturing system of claim 1 wherein the coupling facility is configured to grasp the lancet carrier in a clamping manner prior to the puncture and to release the lancet carrier after the puncturing motion and a returning motion are completed.

7. The puncturing system of claim 1 wherein the coupling facility comprises a spring element configured to effect a clamping force for clamping the lancet carrier.

8. The puncturing system of claim 1 wherein the coupling facility includes a structured contact surface configured to contact the lancet carrier.

9. The puncturing system of claim 8 wherein the structured contact surface is configured to resist a relative motion of the lancet carrier and the structured contact surface with respect to each other, wherein the amount of resistance depends on the direction of the relative motion.

10. The puncturing system of claim 1 wherein the coupling facility has fibers that are obliquely inclined in the direction of motion during retraction of the lancet in the puncturing position.

11. The puncturing system of claim 10 wherein the coupling facility and the lancet carrier combined are configured to provide varying levels of resistance depending on direction of movement of the lancet positioned at the puncturing position.

12. The puncturing system of claim 1 wherein the lancets are oriented transverse to the longitudinal direction of the lancet carrier.

13. A combination of a magazine and a puncturing device, the combination for obtaining a sample of body fluid, the combination comprising:
   the magazine comprising a lancet carrier that carries a plurality of lancets, wherein the magazine is adapted to be inserted into the puncturing device;
   the puncturing device comprising a puncturing drive for accelerating the lancets in a puncturing motion;
   the magazine further comprising a coupling facility for coupling the lancet carrier to the puncturing drive;
   the coupling facility comprising a receptacle defining a recess in which a portion of the lancet carrier is received, the receptacle being mobile with respect to a magazine housing, wherein the receptacle is adapted to couple the puncturing drive to one of the lancets positioned in a puncturing position for transmitting a driving force generated by the puncturing drive during a puncture to the lancet positioned in the puncturing position; and
   wherein the puncturing drive is configured to move the lancet along with the portion of the lancet carrier received in the recess by moving the receptacle in the puncturing motion during the puncture.

14. A magazine for obtaining a sample of body fluid and for removable insertion into a puncturing device, the magazine comprising:
   a lancet carrier including several lancets;
   a coupling facility including a receptacle defining a recess in which a portion of the lancet carrier is received, the recess configured to position one of the lancets in a puncturing position;
   wherein the coupling facility is configured to accelerate the lancet positioned in the puncturing position for a puncture due to a force received from the puncturing device; and
   wherein the lancet along with the portion of the lancet carrier received in the recess are configured to move as the receptacle moves during the puncture.

* * * * *